United States Patent
Hurlimann et al.

(10) Patent No.: US 10,684,236 B2
(45) Date of Patent: Jun. 16, 2020

(54) MICROWAVE MEASUREMENT OF WATER FRACTION

(71) Applicant: SCHLUMBERGER TECHNOLOGY CORPORATION, Sugar Land, TX (US)

(72) Inventors: Martin Hurlimann, Newton, MA (US); Joseph P. Tomanic, Danbury, CT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 555 days.

(21) Appl. No.: 15/111,755

(22) PCT Filed: Jan. 22, 2015

(86) PCT No.: PCT/US2015/012415
§ 371 (c)(1),
(2) Date: Jul. 14, 2016

(87) PCT Pub. No.: WO2015/112688
PCT Pub. Date: Jul. 30, 2015

(65) Prior Publication Data
US 2016/0334343 A1    Nov. 17, 2016

Related U.S. Application Data (60) Provisional application No. 61/930,237, filed on Jan. 22, 2014.

(51) Int. Cl.
*G01R 27/26* (2006.01)
*G01N 22/04* (2006.01)
(Continued)

(52) U.S. Cl.
CPC ............. *G01N 22/04* (2013.01); *E21B 49/08* (2013.01); *E21B 49/082* (2013.01); *E21B 49/10* (2013.01);
(Continued)

(58) Field of Classification Search
CPC ........ G01N 22/04; G01N 22/00; G01N 33/18; G01N 33/2847; E21B 49/08; E21B 49/082; E21B 49/10; E21B 2049/085
(Continued)

(56) References Cited

U.S. PATENT DOCUMENTS

| 5,926,024 A | 7/1999 | Blount et al. |
| 2003/0011386 A1* | 1/2003 | Xie .................. G01N 22/00 324/694 |

(Continued)

FOREIGN PATENT DOCUMENTS

WO    WO03034051 A1    4/2011

OTHER PUBLICATIONS

Afsar, M. N. et al., "The Measurement of the Properties of Materials", Proceedings of the IEEE, 1986, 74(1), pp. 183-199.
(Continued)

*Primary Examiner* — Melissa J Koval
*Assistant Examiner* — Courtney G McDonnough (57) ABSTRACT

Apparatus and methods are provided for finding indications of at least one of a water fraction, a hydrocarbon fraction, water conductivity, and water salinity of a fluid. The fluid is within a flow line that extends through a resonator. The flow line is subjected to microwaves at multiple microwave frequencies injected into the resonator, with electric field lines parallel to the fluid flow line. A power detector is used at an output of the resonator, and a peak power and associated resonance frequency are used to find the indication(s) which may be plotted and displayed. In one embodiment, the
(Continued)

resonator is a dual loop-gap resonator, and the microwave frequencies are generated by a microwave sweeper source at approximately 1 GHz.

28 Claims, 9 Drawing Sheets

(51) Int. Cl.
 E21B 49/10 (2006.01)
 G01N 22/00 (2006.01)
 G01N 33/18 (2006.01)
 E21B 49/08 (2006.01)
 G01N 33/28 (2006.01)

(52) U.S. Cl.
 CPC ............ *G01N 22/00* (2013.01); *G01N 33/18* (2013.01); *G01N 33/2847* (2013.01); *E21B 2049/085* (2013.01)

(58) Field of Classification Search
 USPC .......................................................... 324/634
 See application file for complete search history.

(56) References Cited

U.S. PATENT DOCUMENTS

| | | | |
|---|---|---|---|
| 2003/0151408 A1* | 8/2003 | Kruspe | G01N 24/081 324/303 |
| 2004/0085077 A1* | 5/2004 | Nyfors | G01N 22/00 324/637 |
| 2006/0288782 A1* | 12/2006 | Sawamoto | D21G 9/0009 73/579 |
| 2008/0136409 A1 | 6/2008 | Sen et al. | |
| 2011/0050233 A1 | 3/2011 | Sato | |
| 2013/0285677 A1* | 10/2013 | Hammer | G01N 27/023 324/655 |

OTHER PUBLICATIONS

Bergman, D. J. et al., "Physical Properties of Macroscopically Inhomogeneous Media", Solid State Physics, 1992, 46, pp. 147-269.
Froncisz, W. et al., "The Loop-Gap Resonator: A New Microwave Lumped Circuit ESR Sample Structure", Journal of Magnetic Resonance, 1982, 47(3), pp. 515-521.
Hardy, W. N. et al., "Split-ring resonator for use in magnetic resonance from 200-2000 MHz", , Review of Scientific Instruments, 1981, 52(2), pp. 213-216.
Klein, L. et al., "An Improved Model for the Dielectric Constant of Sea Water at Microwave Frequencies, IEEE Transactions on Antennas and Propagation", AP-25, 1977, 25(1), pp. 104-111.
Mehdizadeh, M. et al., "Loop-Gap Resonator: A Lumped Mode Microwave Resonant Structure", IEEE Transactions on Microwave Theory and Techiques, MTT-31, 1983, 31(12), pp. 1059-1064.
Milton, G. W., "Bounds on the complex permittivity of a two-component composite material", Journal of Applied Physics, 1981, 52(8), pp. 5286-5293.
Sen, P. N. et al., "A self-similar model for sedimentary rocks with application to the dielectric constant of fused glass beads", Geophysics, 1981, 46(5), pp. 781-795.
Shuh-Han, C. "Measurements of Microwave Conductivity and Dielectric Constant by the Cavity Perturbation Method and Their Errors", IEEE Transactions on Microwave Theory and Techniques, MTT-33, 1985, 33(6), pp. 519-526.
Taherian, M. R. et al., "A Coaxial-Circular Waveguide for Dielectric Measurement", IEEE Transacations on Geoscience and Remote Sensing, 1991, 29(2), pp. 321-330.
Tsapin, A. I. et al., "Bimodal Loop-Gap Resonator", Journal of Magnetic Resonance (1969), 1992, 100(3), pp. 484-490.
Wood, R. L. et al., "The loop-gap resonator. II. Controlled return flux-three-loop, two-gap microwave resonators for ENDOR and ESR spectroscopy", Journal of Magnetic Resonance (1969), 1984, 58(2), pp. 243-253.
Saxton, J. A. et al. "Electrical Properties of Sea Water", Wireless Engineer, 1952, pp. 269-275.
Search Report and Written Opinion of International Patent Application No. PCT/US2015/012415 dated May 1, 2015 17 pages.
International Preliminary Report on Patentability of International Patent Application No. PCT/US2015/012415 dated Aug. 4, 2016, 14 pages.

* cited by examiner

MICROWAVE MEASUREMENT OF WATER FRACTION

CROSS-REFERENCE TO RELATED APPLICATIONS

This application claims priority to U.S. Provisional Application No. 61/930,237 filed Jan. 22, 2014, the entire disclosure of which is hereby expressly incorporated by reference herein.

TECHNICAL FIELD

The subject disclosure relates to measuring a property of a fluid within a chamber. More particularly, the subject disclosure relates to measuring an indication of water fraction of a fluid within a chamber.

BACKGROUND

Electromagnetic techniques have been used to distinguish hydrocarbons and water. The methods generally rely on the contrast between the real part of the impedance signal from water and hydrocarbon, as water has a finite conductivity while hydrocarbon has a conductivity close to zero. However, using the real part of the impedance signal, it is not possible to determine the water saturation (fraction) of a hydrocarbon-water mixture from a single conductivity measurement as the conductivity of the water phase must be known independently. In particular, the conductivity of the water phase depends on salinity and can vary by more than a factor of ten.

SUMMARY

Methods and apparatus are provided for measuring the water fraction of a fluid stream containing hydrocarbons and water of unknown salinity using microwave measurements. In one embodiment, microwaves of selected frequencies are injected into a microwave resonator through which a flow line containing the fluid of interest extends, and peak power associated with a corresponding (resonant) frequency exiting the resonator is detected. The peak power and corresponding frequency are then used to find the water concentration (fraction) and the water conductivity.

In one embodiment, a loop-gap (also known as split-ring) resonator is utilized. In one embodiment, the loop-gap resonator is a double loop-gap resonator. In one embodiment, the fluid flow line that extends through the (double) loop-gap resonator is substantially transparent to microwave radiation ("non-conducting").

In one embodiment, microwaves of approximately 1 GHz are injected into the loop-gap resonator. For purposes of the specification and claims, the term "approximately" is to be understood as being ±20%, so that "approximately 1 GHz" shall include a range of 800 MHz to 1.2 GHz. In one embodiment, the microwaves injected into the loop-gap resonator have a range of approximately 10 MHz.

In one embodiment, a cross-plot that transforms the detected peak power and its corresponding frequency directly to water concentration and conductivity is utilized in order to find the water concentration and/or conductivity. In another embodiment, the peak power and corresponding frequency can first be used to determine conductivity of the water, and then the conductivity of the water can be used with the peak power and/or corresponding (resonant) frequency in order to find the water concentration.

Additional aspects, embodiments, objects and advantages of the disclosed methods may be understood with reference to the following detailed description taken in conjunction with the provided drawings.

BRIEF DESCRIPTION OF THE DRAWINGS

FIG. 3d is a partial exploded perspective view of the double loop-gap resonator of FIG. 3a.

DETAILED DESCRIPTION

Illustrative embodiments of the present disclosure are directed to methods and apparatus for measuring an indication of the water fraction of a fluid within a flow line. More particularly, the subject disclosure relates using microwave measurements to determine an indication of the water fraction of a fluid which is comprised of a hydrocarbon fraction and a water fraction of unknown salinity. The subject disclosure has particular application to the hydrocarbon industry and the downhole analysis of fluid flowing through a flow line, although it is not limited thereto.

Before describing the drawings, it is useful to understand some theoretical matters that inform the embodiments. As previously stated, it is not possible to determine the water saturation of a water-oil mixture from a single conductivity measurement alone because the conductivity of the water, which is dependent upon salinity, must be known independently. In contrast, the imaginary part of the impedance depends only little on salinity and other environmental factors such as temperature. However, the dielectric constants of hydrocarbons ($\varepsilon \approx 2$) and water ($\varepsilon \approx 78$) exhibit a large contrast. As a result, the value of the effective dielectric constant of a hydrocarbon-water mixture is mainly a function of the water fraction.

In one aspect, it is noted that the contrast in dielectric constants and conductivity between oil and gas is small compared with the contrast between oil and water ($\varepsilon_{gas} \approx 1$, $\sigma_{gas}=0$; $\varepsilon_{Oil} \approx 2$, $\sigma_{Oil}=0$; $\varepsilon_{H_2O} \approx 78$, $\sigma_{H_2O} \approx 0.1$-$10$ S/m). Thus, the apparatus and method described hereinafter that relies on the contrast in dielectric constants does not easily distinguish between oil and gas, and it is the total volume fraction of hydrocarbons (and water) that is generally determined. However, once the volume fractions of the hydrocarbons and water (and the water salinity) are known, a density measurement may be utilized to distinguish between oil and gas.

In one aspect, multiple considerations should be taken into account when choosing a frequency range of investigation of an oil-water flow line. First, it will be appreciated that it may be desirable to make the loss tangent of the system as small as possible, thereby increasing the sensitivity to the dielectric signal, reducing the amount of heat absorption of the flow line contents, and providing a larger signal for analysis. The loss tangent is defined according to $$\tan\theta = \frac{\sigma_{eff}}{\varepsilon_0 \varepsilon_{eff} \omega}$$

where $\sigma_{eff}$ is the effective conductivity of the fluid mixture, $\omega$ is the vacuum permittivity, $\varepsilon_{eff}$ is the effective dielectric constant of the fluid mixture, and w is angular frequency. At frequencies $f=\omega/2\pi$ below 1 GHz, the effective conductivity $\sigma_{eff}$ is dominated by ionic conduction and is not frequency dependent to a large extent. In this range, the loss tangent is therefore decreasing with increasing frequency. At higher frequencies (e.g., in the high GHz range), dipolar losses become important so that $\tan\theta$ increases with frequency. The loss tangent has therefore a minimum in the GHz frequency range above 1 GHz. At 1 GHz, the loss tangent for 100% water with a conductivity of 10 S/m is $\tan\theta=2.3$. The loss tangents are correspondingly smaller for less saline water and for oil-water mixtures.

It should also be appreciated that the effective conductivity $\sigma_{eff}$ and the effective dielectric constant $\varepsilon_{eff}$ of a mixture do not only depend on the volume fraction of each constituent, but also on its spatial distribution. Exact bounds on $\sigma_{eff}$ and $\varepsilon_{eff}$ for a given water saturation have been derived. See, Milton, G. W., *J Appl. Phys.* 52(8), 5286 (1981). Analysis of these results show that the bounds are much tighter at higher frequencies.

Further, and in accord with one aspect, the skin depth $\delta$ (i.e., the distance that conduction extends into the sample) may be on the order of, or even large relative to the sample size in order for the measurement to represent the whole volume. For salty water (saline) with a conductivity of 10 S/m, the skin depth $\delta=5$ mm at 1 GHz. Less salty water and oil-water mixtures have a larger skin depth. Thus, in order to have a large skin depth relative to the sample size, the sample size should be small (i.e., at least one order of magnitude smaller) compared with the wave length $\lambda$ ($\lambda \geq 30$ cm for a 1 GHz signal). It is noted that this consideration is in distinction to optical measurements where the sample size is typically large compared with the wave length.

In summary, the loss tangent consideration and the tight bounds consideration weigh in favor of using frequencies above 1 GHz, while the skin depth consideration weighs in favor of using a frequency below 1 GHz. As a result, in one embodiment, frequencies of approximately 1 GHz may be considered particularly useful for microwave analysis of a water-hydrocarbon mixture. In other embodiments, frequencies of between approximately 500 MHz and 2 GHz may be considered particularly useful for microwave analysis of a water-hydrocarbon mixture.

According to one aspect, various criteria may be considered in selecting a microwave resonator that will be used to measure the effective dielectric constant and the effective conductivity of a fluid. Where fluid is passed through a microwave cavity and the shift in resonance frequency and line width is monitored (cavity perturbation), the change in the resonance frequency $f_0$ and the line width $\Delta f$ at half maximum power due to the oil-water mixture can be related to the effective dielectric constant $\varepsilon_{eff}$ and effective conductivity $\sigma_{eff}$ to first order according to $$\frac{\delta f_0}{f_0} + j\frac{1}{2}\frac{\delta \Delta f}{f_0} = \left(\varepsilon_{eff} - 1 - j\frac{\sigma_{eff}}{\omega_0 \varepsilon_0}\right) \frac{\varepsilon_0 \int_{flowline} dV(\vec{E}\cdot\vec{E_0^*})}{\int_{Resonator} dV(\vec{D_0}\cdot\vec{E_0^*} + \vec{B_0}\cdot\vec{H_0^*})} \quad (1)$$

where j is the square root of $-1$, dV is the volume element of integration, $E_0$, $D_0$, $B_0$ and $H_0$ are the fields of the unperturbed resonator, and E is the perturbed electric field in the fluid mixture. In equation (1), it is assumed that the magnetic susceptibility $\mu=1$. It will be appreciated that if the electric and magnetic field distribution in the resonator and the geometrical shapes are known, then equation (1) can be used to infer the effective dielectric constant $\varepsilon_{eff}$ and the effective conductivity $\sigma_{eff}$ from measured values of the change in the resonance frequency ($\delta f_0$) and the change in the line width ($\delta \Delta f$). Alternatively, the same information may be obtained by calibrating the system with fluid mixtures of known $\varepsilon_{eff}$ and $\sigma_{eff}$.

In choosing a resonator for cavity perturbation, various considerations are optionally taken into account. First, the size of the resonator may be important in certain circumstances. Thus, where the resonator is to be used downhole in a formation, the resonator cavity is desirably compact and mechanically robust. Second, it may be desirable that the resonator not present large constrictions in the flow path. Third, it may be desirable for the electric fields to have a strength and distribution such that the values for $\delta f_0$ and $\delta \Delta f$ as estimated from equation (1) are in a reasonable range. Fourth, it may be desirable that the electric field lines not intersect the surface of the flow lines. This fourth consideration may be important in reducing or eliminating an issue that arises when the flow line is coated by a layer of oil. In that situation, if the electric field lines are perpendicular (intersect) the oil layer, the oil layer can act as a high impedance in series with the rest of the fluid mixture and can easily dominate the total impedance. In contrast, if the electric field lines are parallel to the oil film, the oil may act as a high impedance in parallel with the rest of the fluid mixture and may have only a small effect on the total impedance. With the electric field lines parallel to the oil film, electric charge will not tend to flow from the electrodes into the fluid and back. Measurements based on such a configuration are sometimes called electrodeless measurements or induction measurements. In such a system, the fluids do not have to be in contact with the metallic parts of the microwave resonator. The fluids can be confined in a non-conducting pipe and the wettability of the pipe can be controlled independently. In addition, problems associated with corrosion may be avoided.

In one embodiment, a microwave resonator useful for measuring water-hydrocarbon mixtures is a fundamental mode resonator with the field pattern $TE_{011}$. It is noted that the $TE_{011}$ fundamental mode resonator can have electric field lines parallel to a fluid flow line. However, the size of the fundamental mode resonator will be on the order of the wavelength, which in the case of a 1 GHZ signal will result in the resonator having a diameter of approximately 36.6 cm. While this may be suitable for uphole analysis, it is generally not suitable for downhole analysis.

Figure 1:
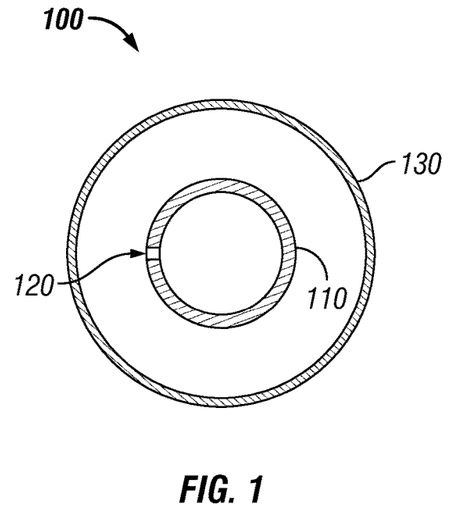
FIG. 1 is a horizontal cross section of a basic loop-gap resonator.

In another embodiment, a microwave resonator useful for measuring water-hydrocarbon mixtures is a loop-gap or split-ring resonator (hereinafter "loop-gap resonator"). A cross-section through a first embodiment of a loop-gap resonator 100 is seen in FIG. 1. Loop-gap resonator 100 includes a pipe 110 cut along its length to define a gap 120, and the pipe 110 is situated inside a can 130. The arrangement of the cut pipe 110 can be thought of as the microwave equivalent of a solenoid, tuned in series with a capacitor. The solenoid consists of a single turn loop and the gap 120 acts as a capacitor. The magnetic field lines are mainly along the axis of the loop and close symmetrically on the outside. The electric fields are concentrated in the gap that forms the capacitor. The whole resonator is surrounded by a metallic can 130 to cut down radiative losses. The resonance frequency of resonator 100 is determined by the loop inductance and the capacitance across the gap and is to first order independent of the length of the resonator. In order to keep end effects to a minimum, the length of the resonator can be longer than the loop diameter. In addition, the length can be much less than the wave length. In one aspect, the gap thickness may be considered to be an important dimension that should be kept constant. Thus, in one embodiment, the gap thickness may be stabilized by inserting a hard, low loss dielectric filler therein, such as quartz or sapphire.

Figure 2:
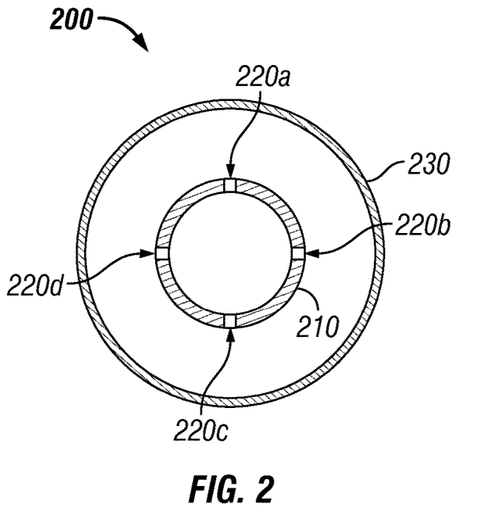
FIG. 2 is a horizontal cross section of a loop-gap resonator with multiple gaps.

With the resonator 100 of FIG. 1, the electric fringe field of the gap 120 may perturb the cylindrical symmetry of the resonator. FIG. 2 shows a horizontal cross section of another loop gap resonator 200 with better cylindrical symmetry. In particular, resonator 200 includes pipe 210 as well as a metallic can 230, with the pipe 210 being cut in four places along its length to provide multiple symmetrical gaps 220a-220d.

Figure 3A:
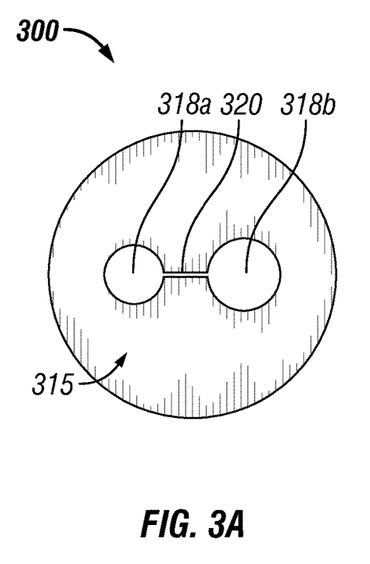
FIG. 3a is a horizontal cross section of a double loop-gap resonator.
Figure 3B:
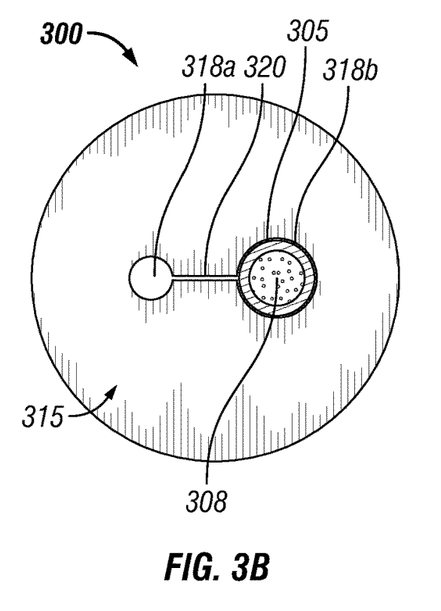
FIG. 3b is a horizontal cross section of the double loop-gap resonator of FIG. 3a with a flow line containing fluid located therein.
Figure 3C:
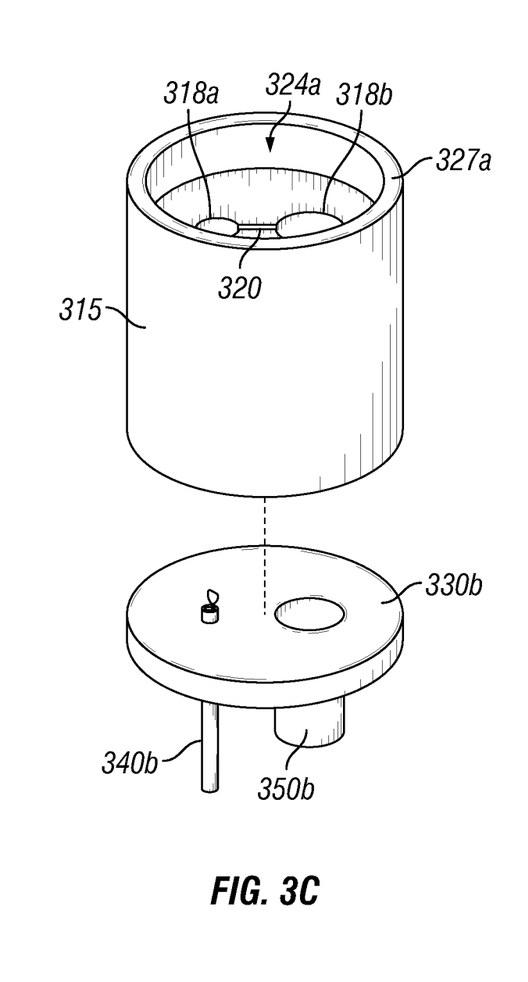
FIG. 3c is a vertical cross section of the double loop-gap resonator of FIG. 3a with a flow line containing fluid located therein.
Figure 3D:
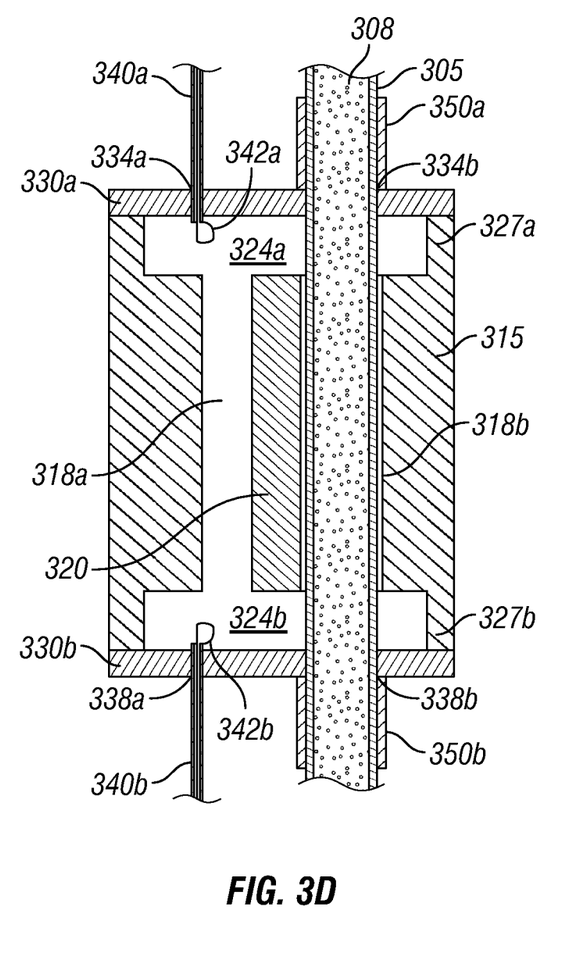

Another embodiment of a loop-gap resonator is seen in FIGS. 3a-3d. FIG. 3a is a horizontal cross section of a double loop-gap resonator 300 while FIG. 3d is a partial exploded perspective view of the double loop-gap resonator 300. FIG. 3b is a horizontal cross section of the double loop-gap resonator of FIG. 3a with a flow line 305 containing fluid 308 located therein, while FIG. 3c is a vertical cross section of the double loop-gap resonator 300 with the flow line 305. As seen in FIGS. 3a-3d, the double loop-gap resonator 300 includes a substantially solid cylindrical metal resonator element 315 that defines first and second hollow pipes 318a, 318b joined by a gap 320, as well as defining upper and lower hollow areas 324a, 324b bound by rims or rings 327a, 327b. Each end of the substantially solid cylindrical resonator element 315 is capped with a metal cap plate 330a, 330b. The cap plates may be of the same diameter as the cylindrical resonator element 315 and are intended to sit atop and seal with the cylindrical resonator element 315.

Each cap plate also defines respective holes 334a, 334b, 338a, 338b for receiving metallic coax cables 340a, 340b, and microwave guide cutoffs 350a, 350b. The microwave guide cutoffs extend from their respective caps away from the cylindrical resonator element 315 and are intended to prevent microwave leakage. The coax cables 340a, 340b extend from outside resonator element 315 to inside the upper and lower hollow areas 324a, 324b of the resonator element 315 and terminate in loops 342a, 342b located in hollow areas 324a, 324b. One coax cable is utilized for injecting microwave energy into the resonator, and the other coax cable is utilized for transmitting microwave energy out of the resonator. The loops 342a, 342b are oriented such that they are at least partially orthogonal to the magnetic field lines.

In one embodiment, by way of example and not by way of limitation, the substantially solid cylindrical element 315 of resonator 300 may be approximately 10 cm in length, and the cap plates 330a, 330b may be approximately 1 to 2 cm in thickness. The lengths of the microwave cut-off guides 350a and 350b may be greater than or equal to the diameter of the hollow pipe 318a (e.g., approximately 3 cm). The diameter of hollow pipe 318a may be approximately in a range from 0.5 to 4 cm, the diameter of hollow pipe 318b maybe in a range from 0.3 to 5 cm, and the gap width may be in a range from 0.1 to 2 mm.

As seen in FIGS. 3b and 3d, a non-metallic flow line 305 extends through the wave guides beyond cutoffs 350a, 350b, holes 338a, 338b in cap plates 330a, 330b, hollow areas 324a, 324b, and hollow pipe 318b. In one embodiment, the flow line 305 has a strongly water-wet coating on the inside to prevent oil from clinging to the circumference of the flow line 305.

In on embodiment, in order to prevent the microwave radiation from leaking out through the flow lines, the diameter d of the flow line 305 may be less than $$d < \frac{0.586c}{f_o\sqrt{\varepsilon}} \approx 2.0 \text{ cm}$$

at a frequency $f_o=1$ GHz and a dielectric constant $\varepsilon=78$ (corresponding to pure water). In one embodiment, this may set an upper limit on the maximum diameter of the flow line. This limit is comparable to a previously mentioned consideration that the diameter of the flow line may be chosen to be on the order of the skin depth δ. For pure water with a conductivity of 10 S/m, δ=5 mm at 1 GHz. For larger flow lines, the frequency can be lowered to avoid microwave radiation leakage from the flow line.

In one embodiment, the resonant frequency and line width of the resonator can be sampled either in reflection or transmission. It is noted that transmission measurements are generally much less sensitive to small discontinuities in the impedances of the whole microwave circuit.

Figure 4:
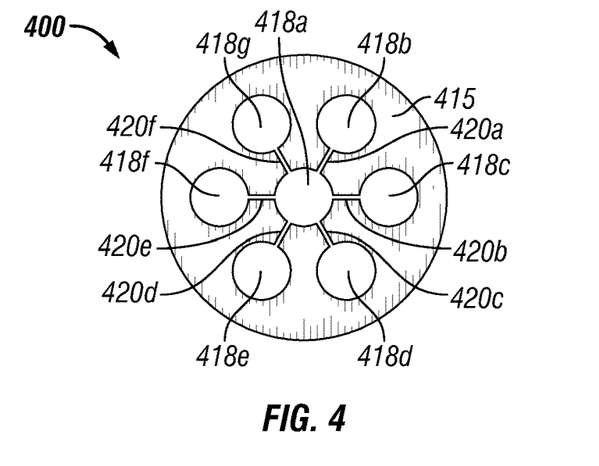
FIG. 4 is a horizontal cross section of a multiple loop-gap resonator.

FIG. 4 is a horizontal cross section of a multiple loop-gap resonator 400. Resonator 400 is similar to resonator 300 except that it is more symmetric and has more than one loop for the flux to return. Thus, resonator 400 includes a substantially solid cylindrical metal resonator element 415 that defines seven hollow pipes 418a-418g with a central hollow pipe 418a joined to the other hollow pipes by gap 420a-420f. One or more of the pipes can carry flow lines. The microwave energy can be injected anywhere, for instance close to one of the pipes unoccupied by a flow line.

Figure 5:
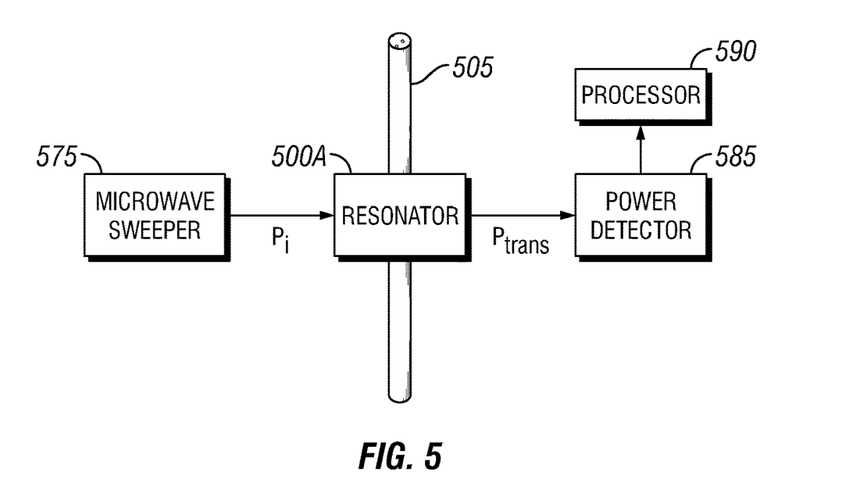
FIG. 5 is a schematic drawing of an apparatus utilizing microwaves and a loop-gap resonator.

Turning now to FIG. 5, a schematic drawing is provided of an apparatus 500 useful in analyzing the content of a fluid flowing in a flow line. The apparatus 500 includes resonator 500A (e.g., a loop-gap resonator), a flow line 505 that extends through the resonator 500A, a microwave sweeper (source) 575 that generates input microwaves of desired frequencies and power ($p_i$) and injects them into the resonator 500A through the microwave coax cable, a detector 585 that detects the power of microwaves transmitted by the resonator 500A, and a processor 590 that processes information provided by the detector 585. In one embodiment the detector is a Schottky diode. In another embodiment, the detector is a tunnel diode detector. In another embodiment, the detector is a network analyzer incorporating coherent detection. A power transmission coefficient trans $P_{trans}/P_i$ is measured over a relatively small frequency range so that it covers frequency shifts due to the mixture in the flow line. According to one aspect, no phase shift measurements are needed. This simplifies the required microwave equipment and the associated costs. In addition, according to another aspect, the measurement is much less sensitive to slight changes in the electrical lengths of the coaxial cables leading to and from the resonator, that can be caused, for instance, by temperature fluctuations.

In principle, it is also possible to make the measurement using the reflection coefficient $P_{ref}/P_i$. However, this measurement is sensitive to small standing waves caused by slight impedance mismatches. While a calibration could be used to correct for the impedance mismatches, they might be dependent on temperature and other environmental effects. The transmission coefficient is much less sensitive to these problems.

The line shape of $P_{trans}$ $P_i$ versus frequency is expected to be Lorentzian:

$$\frac{P_{trans}}{P_i}(f) = \frac{P_0}{1 + 4\left(\frac{f - f_0}{\Delta f}\right)^2} \quad (2)$$

Three parameters are required to describe the line shape: $f_o$, the resonance frequency where the transmitted power is maximal; $P_o$, the maximal transmitted power; and $\Delta f$, the line width. At $f = f_o \pm \Delta f/2$, the transmitted power equals $P_o/2$. However, as described hereinafter, it is not necessary to perform a three parameter fit to obtain $f_o$ and $\Delta f$. Rather, for a given resonator, there is a one to one relationship between $P_o$ and $\Delta f$. It is sufficient to measure the frequency and power level where maximal power transmission occurs which may be considered to be a very simple measurement.

Figure 6:
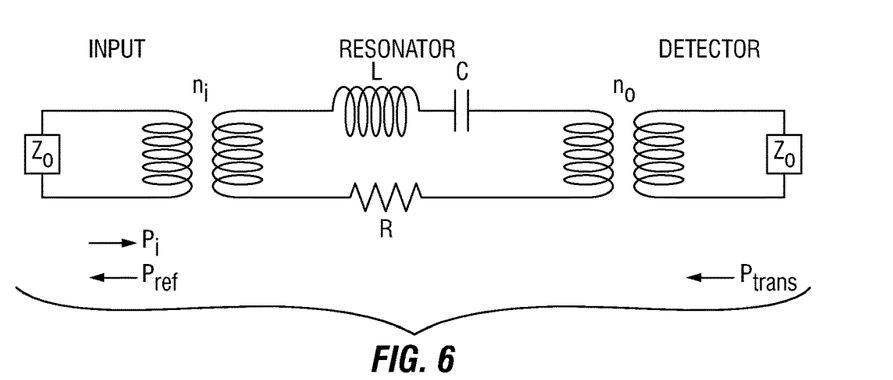
FIG. 6 is an equivalent circuit diagram for the schematic drawing of FIG. 5.

The relationship between $P_o$ and $\Delta f$ can be derived with the equivalent circuit shown in FIG. 6. It is assumed that the microwave source and detector have a characteristic impedance $Z_o$ and that the magnetic coupling can be represented by the transformer with turns ratio $n_i$ and $n_o$. The coupling is adjusted to be in the limit of a weak coupling: $Z_o \ll 2\pi n_i^2 L \Delta f$ and $Z_o \ll 2\pi n_o^2 L \Delta f$. The fluid mixture will change the effective resistance R and capacitance C of the resonator. In terms of the lumped circuit elements, the resonance frequency and the line width are given by:

$$f_o = \frac{1}{2\pi\sqrt{LC}}, \Delta f = \frac{R}{2\pi L} \quad (3)$$

In the limit of weak coupling, the power transmission coefficient can be derived according to:

$$\frac{P_{trans}}{P_i}(f) = \frac{Z_o^2}{\pi^2 n_o^2 n_i^2 L^2} \frac{1}{(\Delta f)^2} \frac{1}{1 + 4\left(\frac{f - f_0}{\Delta f}\right)^2} \quad (4)$$

A comparison between equations (2) and (4) shows that the maximal transmitted power $P_o$ is (inversely) proportional to $(\Delta f)^2$:

$$P_o = \frac{Z_o^2}{\pi^2 n_o^2 n_i^2 L^2} \frac{1}{(\Delta f)^2} \quad (5)$$

Equation (5) implies that the resonance frequency $f_o$ and the line width $\Delta f$ can be simply determined by a peak detector. The frequency of the peak is $f_o$, and from the peak power $P_o$, $\Delta f$ can be determined by equation (5).

Using the loop-gap resonator of FIGS. 3a-3d, measurements were made on mixtures of dodecane and water with different salinities. The water saturation was changed between 0 and 100% and the water conductivity varied between 1 S/m and 10 S/m. The dimensions of the resonator were chosen such that the resonance frequencies varied over a range from about 986 MHz to 994 MHz, a range of less than 1%.

Figure 7:
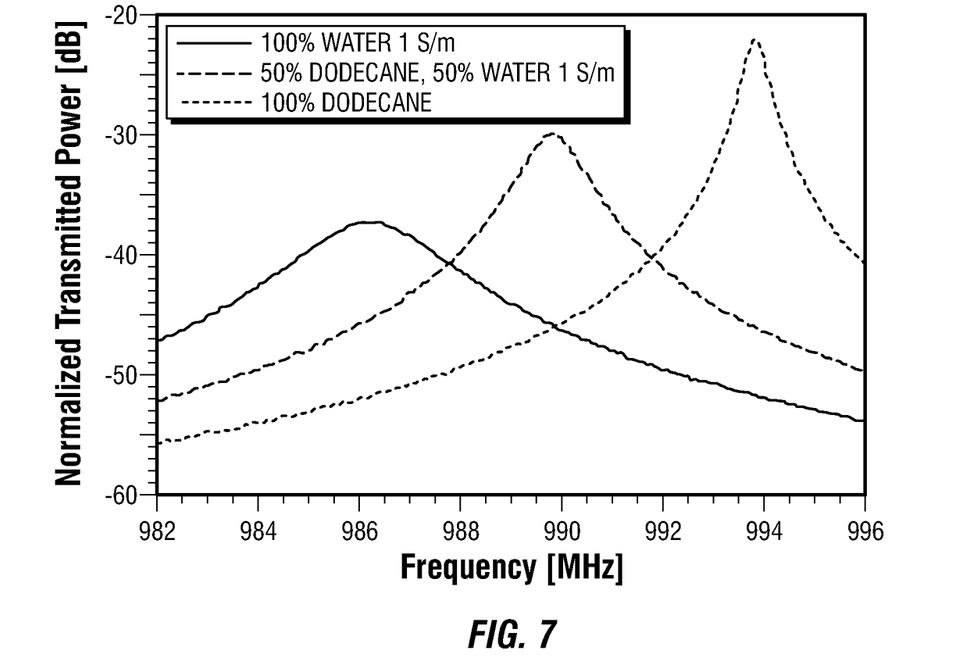
FIG. 7 is a diagram plotting normalized transmitted power versus frequency for pure water of a first conductivity, 50% dodecane and 50% water of the first conductivity, and 100% dodecane.
Figure 8:
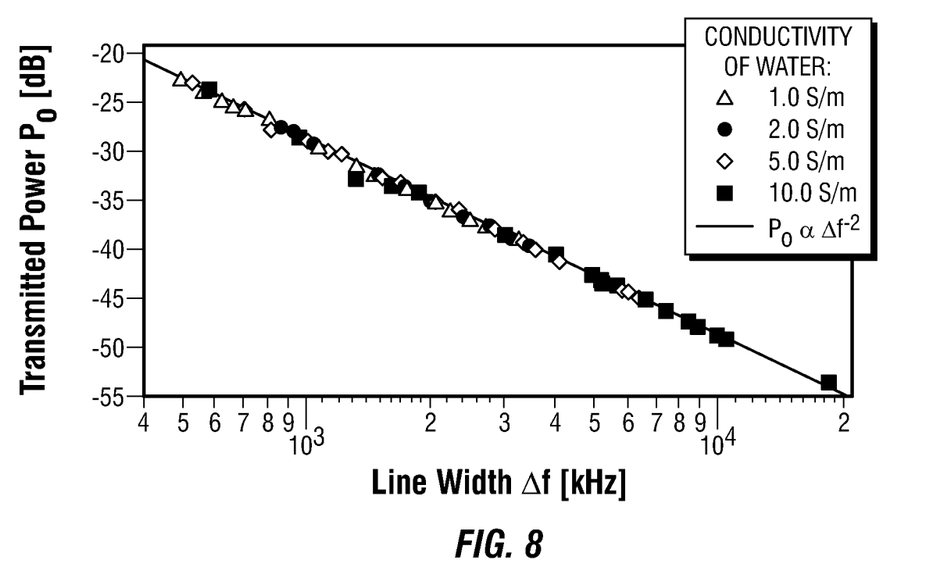
FIG. 8 is a diagram plotting transmitted power versus line width for water samples of different conductivities.

FIG. 7 show representative examples of the normalized transmitted power $P_{trans}/P_i$ versus frequency between 982 MHz and 996 MHz for three different fluid mixtures (pure water of a first conductivity, 50% dodecane and 50% water of the first conductivity, and 100% dodecane) in the flow line together with a fit to a Lorentzian line shape. The fits are excellent. FIG. 8 shows the measured relationship between the transmitted power at the maximum, $P_o$, and the line width $\Delta f$ for many different mixtures. As predicted by equation (5), $P_o$ is proportional to $\Delta f^2$ over the whole range, which spans approximately three decades in power.

Figure 9A:
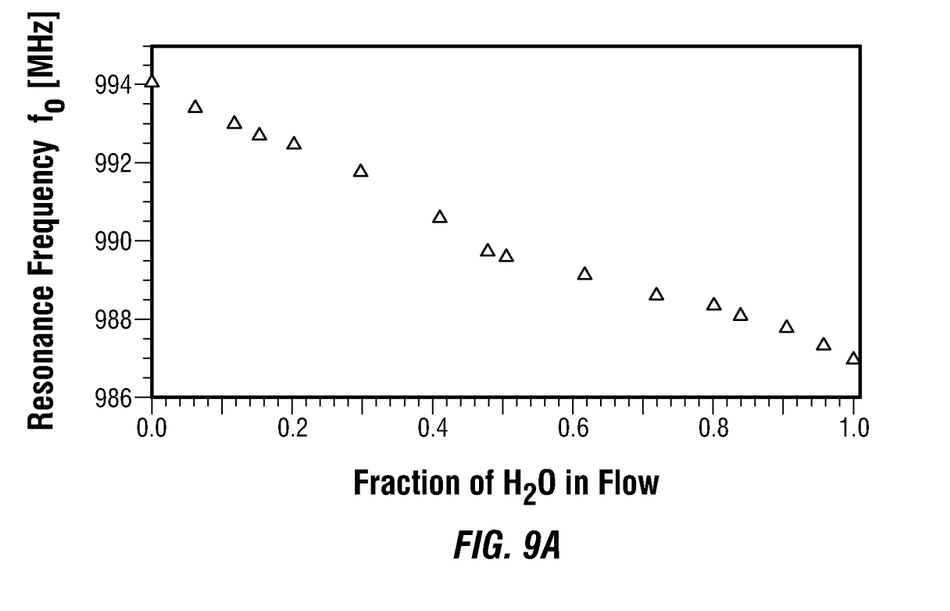
FIG. 9a is a plot of resonance frequency versus water fraction for water of a particular conductivity.
Figure 9B:
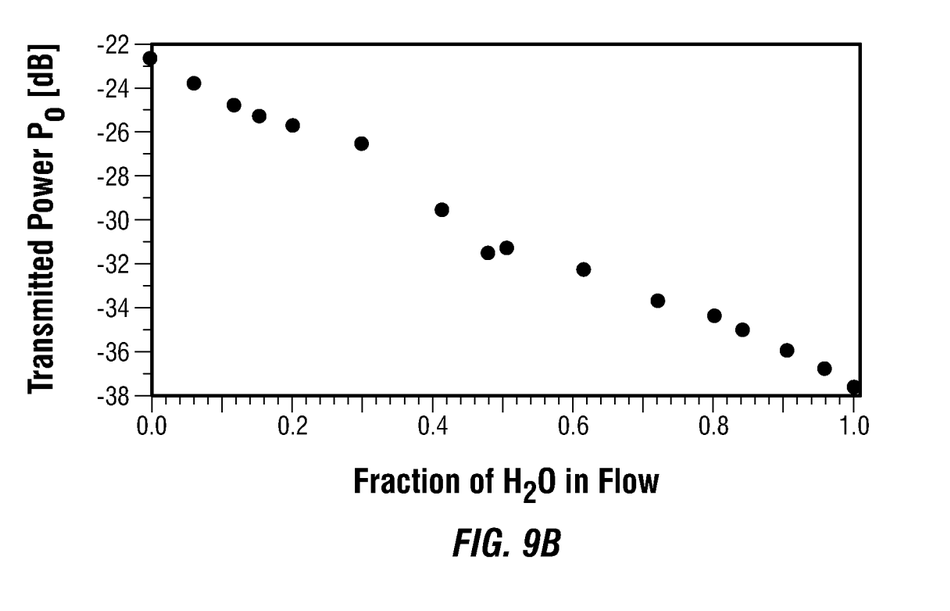
FIG. 9b is a plot of transmitted power versus water fraction for water of a particular conductivity.

For the double loop-gap resonator used in generating FIGS. 7 and 8, the distribution of electric and magnetic fields were not calculated exactly. For this reason, it is useful to calibrate the resonator experimentally. In FIGS. 9a and 9b, calibration curves obtained with water that has a conductivity of 1 S/m are shown. In FIG. 9a, the resonance frequency $f_o$ is displayed versus the water concentration. In FIG. 9b, $P_o$ is plotted versus water concentration. The calibration may be repeated for the whole range of water salinities expected to be encountered. This is particularly useful where the skin depth at the highest conductivity is smaller than the diameter of the flow line.

The influence of different spatial arrangements of oil and water was also investigated. The variety of arrangements leads to a broadening of the calibration curves (such as FIGS. 9a and 9b). In particular, the flow line in the experimental arrangement had no special coating so that both water and oil bubbles could stick to it. This results in different fluid distribution inside the line, depending on the history of the flow. In addition, the fluid distribution depends on the flow velocity. In some embodiments, the measurement is made while the fluid is not flowing. In other embodiments, the measurement is made while the fluid is flowing within the flow line. In an experiment, the fluid distribution inside the flow line was changed by continuously changing the oil to water ratio and the flow velocity.

Figure 10:
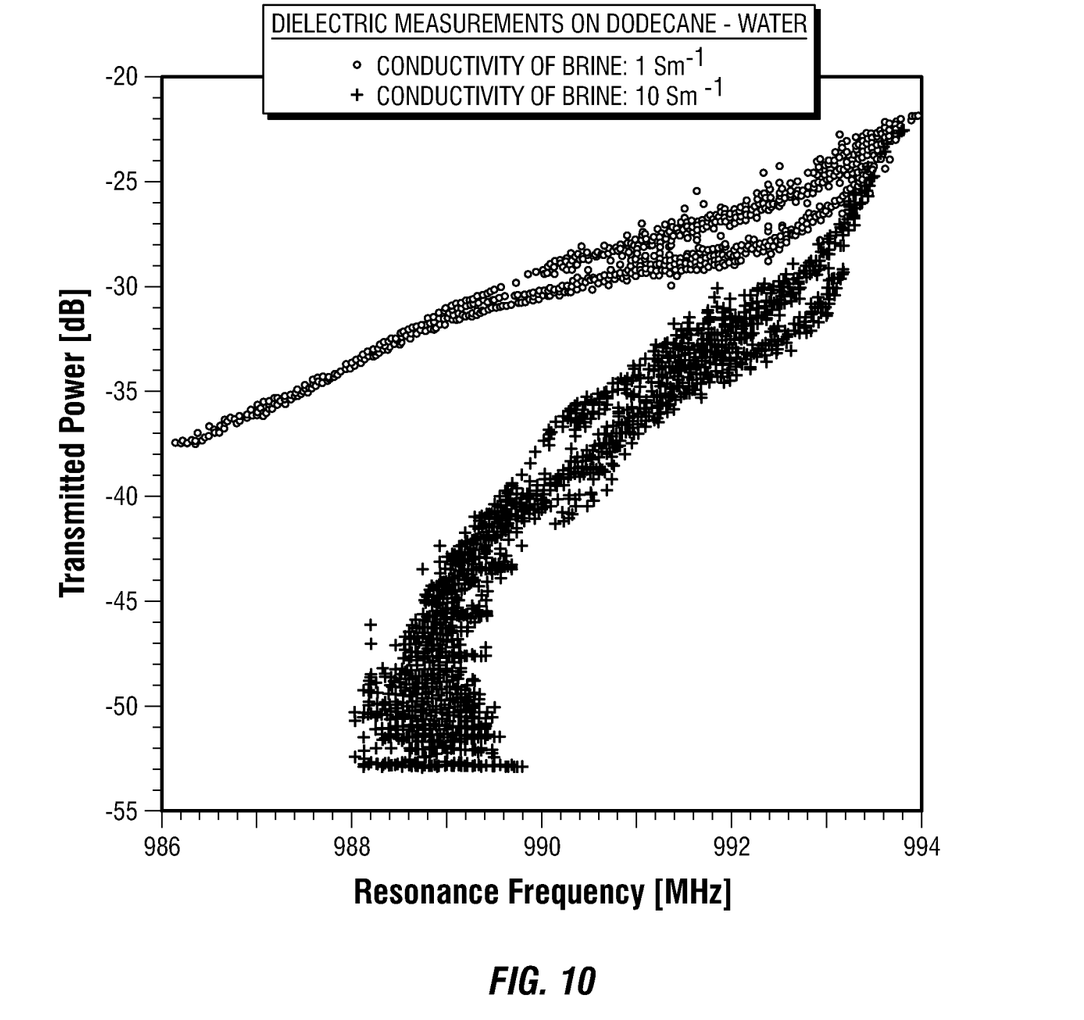
FIG. 10 is a cross plot of transmitted power versus resonance frequency for samples containing different hydrocarbon-water ratios at two different water conductivities.

The experiment was repeated with water of different conductivity (i.e., 1 S/m and 10 S/m). Every 0.25 second, a spectrum similar to the one shown in FIG. 7 was recorded, and the peak power $P_o$ and corresponding frequency $f_o$ were found. A plot of the results is seen in FIG. 10, where the peak power $P_o$ is plotted against the frequency $f_o$ for both experiments. The data is seen to lie in two bands with some finite width. It is noted that the two bands are not overlapping, except at the upper right corner, which corresponds to 100% oil. It is also noted that repeating the experiments with water of different conductivity would result in the generation of other bands. This plot therefore demonstrates that from a simple measurement of the peak power $P_o$ and the corresponding frequency $f_o$, the conductivity of the water may be estimated. Then, using a calibration curve for the conductivity (e.g., FIG. 9a or 9b), the water concentration (fraction) can be determined. Alternatively, a map can be constructed that transforms $P_o$ and $f_o$ directly onto water concentration and conductivity.

Figure 11:
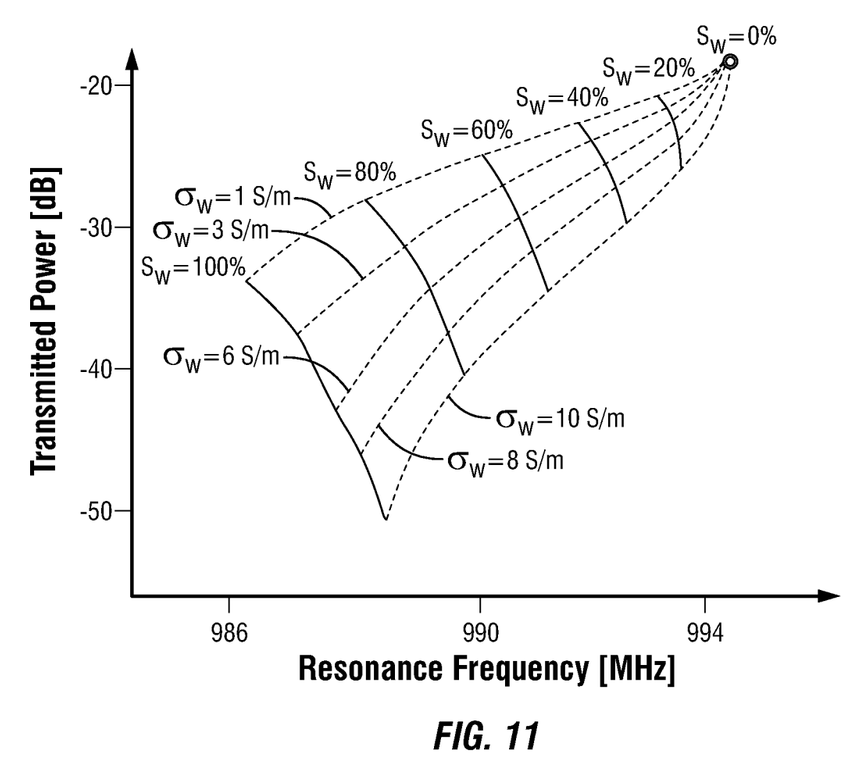
FIG. 11 is a cross plot of transmitted power versus resonance frequency from which water concentration and conductivity may be directly obtained.

FIG. 11 is a cross plot of resonance frequency versus transmitted peak power from which water concentration (fraction) and conductivity may be directly obtained. While five dotted lines corresponding five different conductivities (1, 3, 6, 8 and 10 S/m), and five solid lines corresponding to five different water saturations (100%, 80%, 60%, 40%, 20%) are shown, with all dotted lines meeting at a point corresponding to water saturation of 0% (all oil), it will be appreciated that all points on the peak power-resonant frequency plot correspond to a particular water saturation with a particular conductivity. It will be appreciated that whether or not a point falls on the shown dotted and/or solid lines, the resulting determination will be an estimation which gives an approximate value for water saturation and conductivity.

According to one embodiment, the information from which FIG. 11 was generated may be stored in a memory as a lookup table of desired granularity. Thus, upon finding a transmitted peak power value and a corresponding resonance frequency, the closest peak power value and frequency value stored in the lookup table will yield a water saturation and conductivity estimate. Similarly, a lookup table with transmitted peak power value and corresponding resonance frequency mapped to conductivity (as in FIG. 10), and a series of lookup tables for different conductivities relating water fraction to resonance frequency (FIG. 9a) and/or relating water fraction to transmitted peak power (FIG. 9b) may be provided. In that case, using the transmitted peak power and corresponding resonance frequency, an estimate of conductivity may be found using a first lookup table, and then using the appropriate second lookup table for that conductivity, the water fraction may be found.

It will be appreciated that wherever a water fraction is estimated, a result is that a hydrocarbon fraction (1-water fraction) is similarly implied. Thus, it is to be understood that a hydrocarbon fraction should be considered to be an "indication" of the water fraction and vice versa. Likewise, wherever conductivity is found, salinity is similarly implied. Thus, it is to be understood that conductivity is an "indication" of salinity and vice versa. In addition, it is to be understood that the lookup tables may be arranged to take the peak power value and corresponding resonance frequency and generate one or more of a water fraction, a hydrocarbon fraction, water conductivity, and water salinity. If an independent fluid density measurement is available, the hydrocarbon fraction may be divided into an oil fraction and a gas fraction in manners well known in the art.

In one embodiment, an apparatus including a microwave source that generates multiple microwave frequencies, a loop-gap resonator having a flow line extending therethrough, and a power detector is located downhole in a formation (e.g., in a wellbore). For purposes herein, the term "wellbore" shall be understood broadly to include uncased wellbores, cased wellbores, producing wells, etc. The apparatus may be fixed (permanent) in the wellbore or may be movable within the wellbore. If movable in the wellbore, the apparatus may be part of a tool that is in fluid communication with the formation. The apparatus is coupled to a power source that may be located downhole and/or uphole. The power detector and the microwave source may be coupled to a processor located downhole and/or uphole. As the microwave source outputs different wavelengths, the power detector detects the output power so that the resonant frequency is known when the peak power is found by the detector. In particular, the injection frequency at the time of peak power output by the power detector may be taken as the resonant frequency. In another embodiment, a peak power detector may be utilized and synchronized with the microwave source such that the microwave source frequency at the time of peak power indication is known. In one embodiment, the processor may utilize one or more lookup tables such as previously described with reference to FIG. 11 or FIGS. 9a, 9b and 10 from which an estimate of at least one of the water fraction, hydrocarbon fraction, water salinity, and water conductivity may be generated based on the peak power and the resonant frequency. According to one aspect, the lookup tables may be implemented in any desired manner in memory. The generated estimates may be plotted on a screen or on paper as a function of time. In another embodiment, rather than utilizing lookup tables, the peak power and the resonant frequency may be plotted onto a cross-plot such as shown in FIG. 11 (or FIG. 10) from which an estimate of at least one of the water fraction, hydrocarbon fraction, water salinity, and water conductivity may be generated. If a cross-plot such as FIG. 10 is utilized to obtain water conductivity, water fraction and/or hydrocarbon fraction may then be generated using the resulting water conductivity to identify an appropriate cross-plot such as FIG. 9a or 9b and utilizing that cross-plot to generate an estimate of water and/or hydrocarbon fraction.

In one embodiment, the apparatus that is located downhole or another substantially identical apparatus is calibrated in order to generate the information for the one or more lookup tables prior to the apparatus being located downhole.

In one embodiment, the loop-gap resonator of the apparatus located in the wellbore may be a double or multiple loop-gap resonator. In one embodiment, the loop-gap resonator of the apparatus is operated at approximately 1 GHz. In one embodiment, the diameter of the flow line extending through the resonantor is small compared with the wave length of the microwave input signal. In one embodiment the diameter of the flow line for an approximately 1 GHz signal is approximately 2.0 cm or smaller. In one embodiment, the flow line through which the fluid flows is oil-wet.

In one embodiment, the microwave source is a microwave sweeper that can sequentially generate microwaves of different frequencies. In one embodiment, the frequency sweep of the input microwave signal is approximately 10 MHz or less. In another embodiment, the microwave source incorporates multiple sources of different microwave frequencies that may be sequentially fed to the resonator.

Figure 12A:
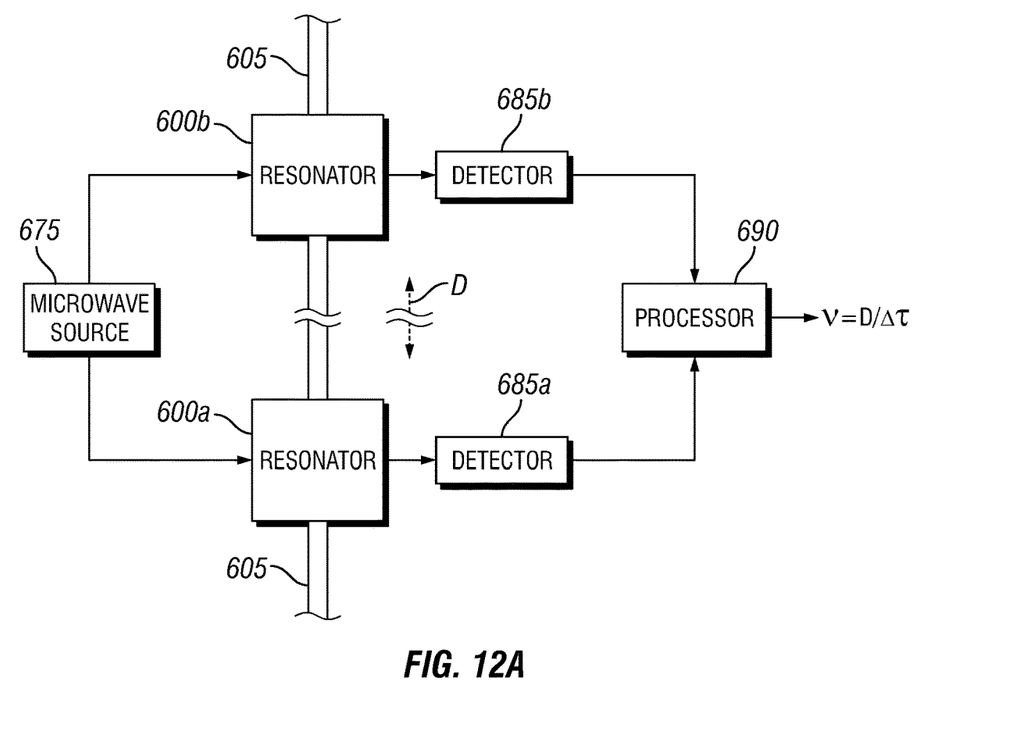
FIG. 12a is a schematic of a system utilizing loop-gap resonators in series.

In one embodiment seen schematically in FIG. 12a, two substantially identical resonators 600a, 600b separated by a distance D are placed in series, and a single flow line 605 is run through both of the resonators. A single microwave source 675 may be used to provide identical signal inputs to both resonators, and measurements are made with respect to each resonator by detectors 685*a*, 685*b* and provided to a processor 690 to determine estimates over time at each resonator of at least one of the water fraction, hydrocarbon fraction, water salinity, and water conductivity of the fluid. If there is significant temporal fluctuation, the two measurements can be correlated, typically using the processor 690. From the time shift $\Delta\tau$, an average velocity $v=D/\Delta T$ of the fluid mixture is obtained. This assumes that there is no significant slippage between the two fluids.

Figure 12B:
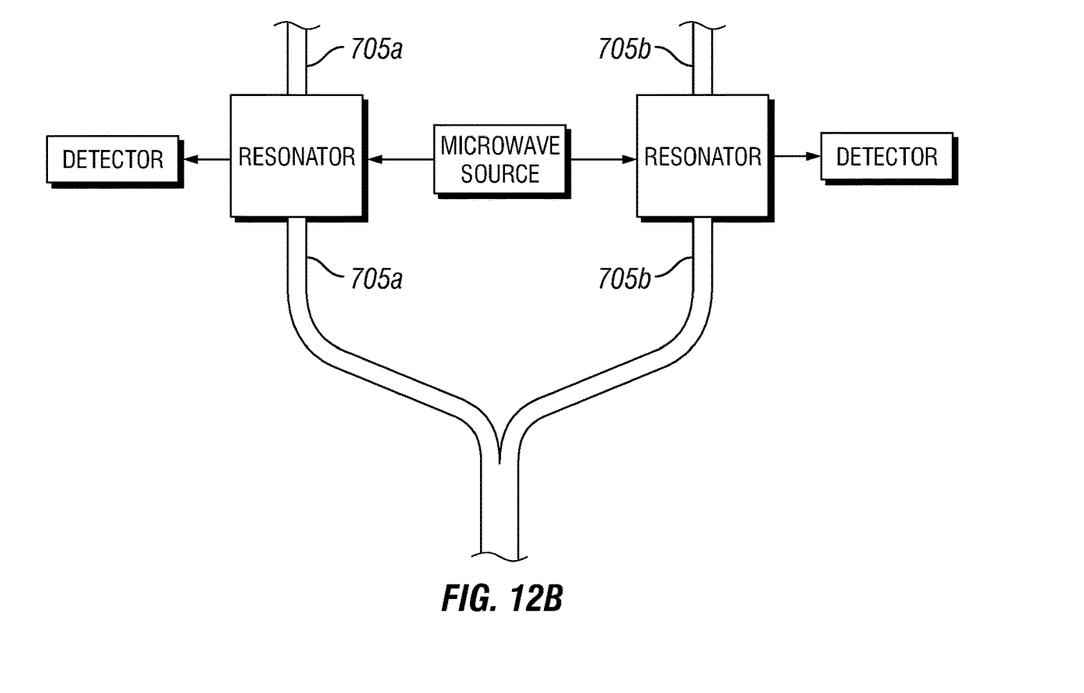
FIG. 12b is a schematic of a system utilizing loop-gap resonators in parallel.

In one embodiment seen schematically in FIG. 12*b*, a plurality of loop-gap resonators (two shown) 700*a*, 700*b* may be used in parallel to increase flow path (i.e., multiple flow paths 705*a*, 705*b* are provided). A single microwave source 775 may be used for the plurality of resonators. Each resonator includes its own detector 785*a*, 785*b*.

In one aspect, the estimate of at least one of the water fraction, hydrocarbon fraction, water salinity, and water conductivity may be generated in real time, which for purposes herein shall mean on the order of seconds (as opposed to recording measurements for processing hours or days later.

In another embodiment, an apparatus includes a microwave source that generates multiple microwave frequencies, a resonator having a flow line extending therethrough and having electric field lines parallel to a fluid flow line, and a (peak) power detector, with the resonant frequency being the injected source frequency at the time of peak power output. The apparatus is coupled to a power source and may be coupled to a processor. In one embodiment, the processor may utilize one or more lookup tables such as previously described with reference to FIG. 11 or FIGS. 9*a*, 9*b* and 10 from which an estimate of at least one of the water fraction, hydrocarbon fraction, water salinity, and water conductivity may be generated based on the peak power and the resonant frequency. According to one aspect, the lookup tables may be implemented in any desired manner in memory. The generated estimates may be plotted on a screen or on paper as a function of time.

Figure 13:
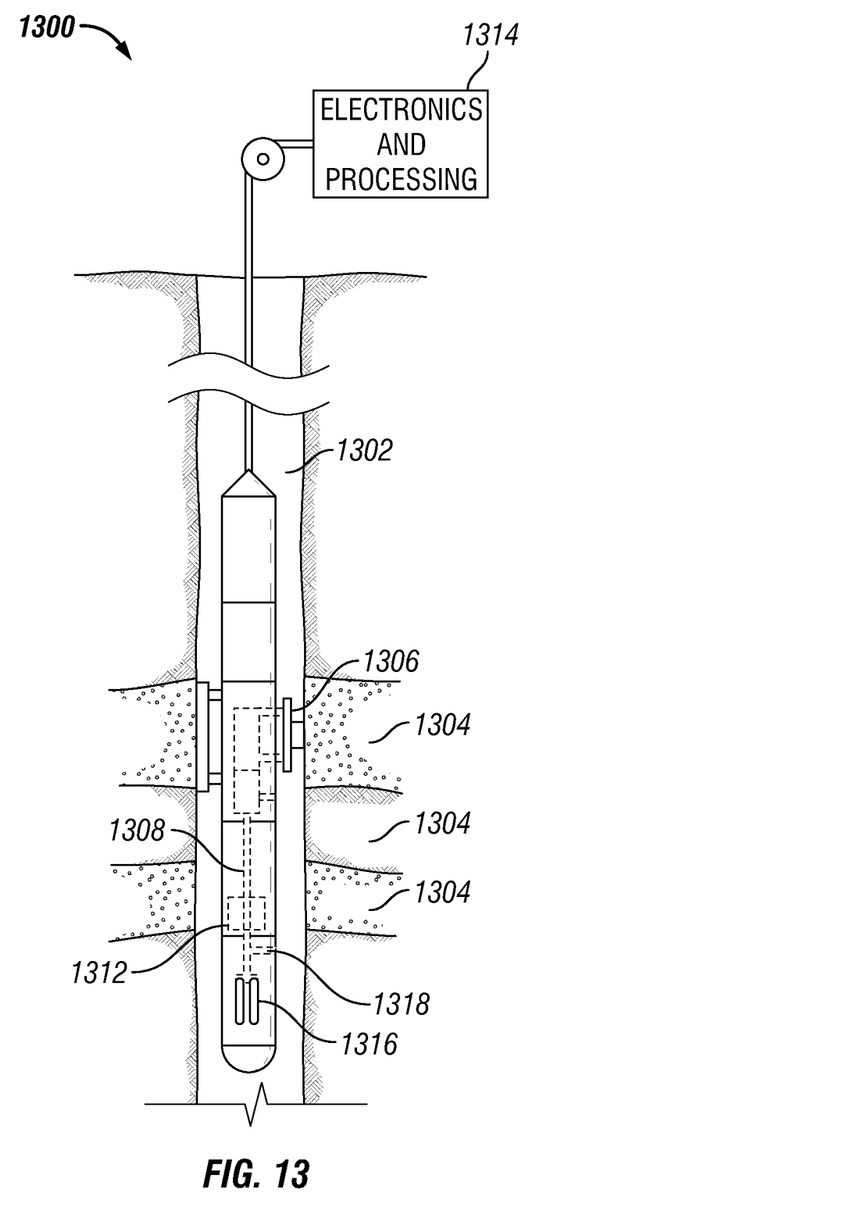
FIG. 13 is a schematic diagram that shows a wellbore tool for analyzing a formation fluid.

Turning to FIG. 13, a schematic diagram shows a wellbore tool 1300 for analyzing a formation fluid. In particular, the wellbore tool 1300 determines a property of the formation fluid within a flow line, such as water fraction, which can then be used to determine, for example, the presence of fractures or other high permeability streaks within the formation.

In this example, the wellbore tool 1300 is a wireline tool. The wireline tool 1300 is disposed within a wellbore 1302 that traverses a formation 1304. The wireline tool includes 1300 a formation fluid testing module, such as the Modular Formation Dynamics Tester™ (MDT) module of Schlumberger. The formation fluid testing module includes a selectively extendable fluid admitting assembly (e.g., probe) 1306. This assembly 1306 extends into contact with the formation 1304 and withdraws formation fluid from the formation 1304 (e.g., samples the formation). The fluid flows through the assembly 1306 and into a flow line 1308 within a housing 1309 of the tool 1300. A pump module (not shown) is used to withdraw the formation fluid from the formation 1304 and pass the fluid through the flow line 1308.

The wireline tool 100 also includes an apparatus 1312 for analyzing the formation fluid within the flow line 1308. The apparatus 1312 includes a microwave source, one or more resonators, and one or more power detectors. As described in the present disclosure, the apparatus 1312 can be used to determine, for example, a water fraction, a hydrocarbon fraction, a water conductivity, and/or a water salinity of the formation fluid within the flow line.

The wireline tool 1300 may contain a processor or processors for processing measurements and generating values for the water fraction, the hydrocarbon fraction, the water conductivity, and/or the water salinity of the formation fluid within the flow line. Alternatively or in addition, a processor or processors 1314 may be located uphole, and signals may be sent from the wireline tool 1300 uphole for processing.

After passing through apparatus 1312, the formation fluid (e.g., the hydrocarbon sample) may be pumped out of the flow line 1308 and into the wellbore 1302 through a port 1318. Some of the formation fluid may also be passed to a fluid collection module 1316 that includes chambers for collecting fluid samples and retaining samples of the formation fluid for subsequent transport and testing at the surface (e.g., at a testing facility or laboratory).

The methods and apparatus described herein can be implemented by various other wellbore tools and wellbore tool configurations. For example, the methods and apparatus described herein can be implemented by a wellbore tool that is conveyed by other means, such as coiled tubing. Furthermore, the methods and apparatus described herein can be applied in logging-while-drilling (LWD) operations, sampling-while-drilling operations, measuring-while-drilling operations, or any other operation where monitoring or logging of formation fluid is performed. Also, the methods and apparatus described herein can be implemented by a wellbore tool that is implemented as part of a completion. The wellbore tool may be disposed within a wellbore as part of a completion and can be used to monitor formation fluids as they flow through the wellbore (e.g., to the surface). For example, a microwave apparatus, according to the present disclosure, can be installed within each stage of a completion. At each stage, the microwave apparatus will monitor local influx of water. If the watercut is too high, this information from the microwave apparatus would then be used to shut off a particular stage of the completion using a valve, while valves in other stages of the completion remain open.

Furthermore, in some embodiments, the methods described herein are implemented within a wellbore. In other embodiments, the methods and apparatus described herein are performed at the surface within a flow line. For example, the methods and apparatus described herein can be performed in a flow line, such as a pipeline transporting fluids (e.g., hydrocarbons and/or water) from a well site or to a refinery. Also, the methods and apparatus described herein have application outside the oilfield. For example, the methods and apparatus described herein can be used in chemical production, food production, material inspection, or any other field where monitoring of fluids within flow lines is performed.

Also, the methods and apparatus described herein are not limited to an implementation that uses a flow line. A chamber having any configuration or geometry can be used. The chamber can be a hollow container or flow line (e.g., pipe) that at least partially contains the fluid. Some of the embodiments described herein may include multiple chambers of the same or different type.

In one aspect, some of the methods and processes described above are performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCM-CIA card), or other memory device.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Thus, by way of example only, and not by way of limitation, while various embodiments describe loop-gap resonators with particular microwave input and output elements, and of particular dimensions and materials, it will be appreciated that other resonators could be utilized, and the input and output elements, dimensions, and materials may be varied. Also, by way of example only, and not by way of limitation, rather than utilizing a peak power detector, it may be possible to find the peak power and resonant frequency by analysis of a resonance curve output by a power detector. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. An apparatus for analyzing a fluid, comprising:
a microwave source that radiates multiple microwave frequencies;
a first chamber for containing the fluid;
a first resonator having the first chamber extending therethrough, wherein the first resonator has a microwave input and a microwave output coupled to the microwave source;
a first power detector coupled to an output of the first resonator and providing a first output power signal; and
a processor coupled to the power detector that generates an indication of at least one of a water fraction, a hydrocarbon fraction, water conductivity, and water salinity of the fluid using a peak power value determined from the first output power signal and a resonance frequency corresponding to the peak power.

2. An apparatus according to claim 1, wherein:
the first chamber is a first flow line and the first flow line, the first resonator, and the microwave source are arranged so that electric field lines generated by the microwave source are parallel to the first flow line.

3. An apparatus according to claim 2, wherein:
the first resonator is loop-gap resonator.

4. An apparatus according to claim 1, wherein:
the multiple microwave frequencies are frequencies greater than approximately 500 MHz and less than approximately 2 GHz.

5. An apparatus according to claim 2, wherein:
the diameter of the first flow line is less than approximately 2 cm.

6. An apparatus according to claim 3, wherein:
the loop-gap resonator is a double loop-gap resonator defining first and second cylinders and a gap coupling the first and second cylinders, with the first chamber extending through the first cylinder and the multiple microwave frequencies being injected into the second cylinder.

7. An apparatus according to claim 1, wherein:
the indication of at least one of a water fraction, a hydrocarbon fraction, water conductivity, and water salinity comprises an indication of water conductivity and an indication of water fraction.

8. An apparatus according to claim 1, further comprising:
a lookup chart associated with the processor, the lookup chart associating peak power and resonance frequency with the indication of at least one of a water fraction, a hydrocarbon fraction, water conductivity, and water salinity.

9. An apparatus according to claim 8, wherein:
the lookup chart associates peak power and resonance frequency with the indication of water fraction and water conductivity.

10. An apparatus according to claim 1, further comprising:
a display that displays the indication of at least one of a water fraction, a hydrocarbon fraction, water conductivity, and water salinity of the fluid as a function of time.

11. An apparatus according to claim 1, wherein:
the first chamber is substantially transparent to the multiple microwave frequencies.

12. An apparatus according to claim 1, wherein:
the microwave source is a microwave sweeper source, and the power detector is a peak power detector.

13. An apparatus according to claim 2, further comprising:
a second flow line;
a second resonator having the second flow line extending therethrough, the second resonator having a microwave input and a microwave output coupled to the microwave source, wherein the second flow line, the second resonator, and the microwave source are arranged so that electric field lines generated by the microwave source are parallel to the second chamber; and
a second power detector coupled to an output of the second resonator and generating a second output power signal, wherein the processor is coupled to the second power detector, and the second flow line and the second resonator are in parallel with the first flow line and the first resonator.

14. An apparatus according to claim 2, further comprising:
a second resonator in series with and separated by a distance from the first resonator, the first flow line extending into through the second resonator;
a second power detector coupled to an output of the second resonator and generating a second output power signal, wherein the processor (i) is coupled to the second power detector, (ii) determines an estimate of at least one of the water fraction, hydrocarbon fraction, water salinity, and water conductivity using a signal from the second output power signal, (iii) correlates the determinations from the first and second output power signals, and (iv) finds a velocity of the fluid based on the distance and the correlation.

15. An apparatus according to claim 1, wherein:
the apparatus is a wellbore tool.

16. A wellbore tool for analyzing a fluid, comprising:
a sweeper microwave source that radiates multiple microwave frequencies in a range of at most approximately 10 MHz at a frequency of approximately 1 GHz;
a flow line for containing the fluid;
a dual-gap resonator defining first and second cylinders and a gap connecting the first and second cylinders, a first of the cylinders having the flow line extending therethrough, and a second of the cylinders receiving the multiple microwave frequencies;
a power detector coupled to the second cylinder of the dual-gap resonator; and
a processor coupled to the power detector that generates an indication of at least one of a water fraction, a hydrocarbon fraction, water conductivity, and water salinity of the fluid from a peak power value of the power detector and a resonance frequency corresponding to the peak power.

17. A wellbore tool according to claim 16, further comprising:
a lookup chart associated with the processor, the lookup chart associating peak power and resonance frequency with the indication of at least one of a water fraction, a hydrocarbon fraction, water conductivity, and water salinity.

18. A wellbore tool according to claim 17, wherein:
the lookup chart associates peak power and resonance frequency with the indications of water fraction and water conductivity.

19. A wellbore tool according to claim 16, wherein:
the wellbore tool is one of a wireline tool, a logging-while-drilling tool, and a completions tool.

20. A method of analyzing a fluid, comprising:
flowing the fluid through a chamber in a resonator;
radiating the chamber in the resonator with microwaves from a microwave generator having multiple microwave frequencies such that electric field lines generated by the microwave generator are parallel to fluid flow in the chamber;
detecting a peak power of the resonator and finding a resonant frequency corresponding to the peak power; and
using the peak power and resonant frequency to generate an indication of at least one of a water fraction, a hydrocarbon fraction, water conductivity, and water salinity of the flowing fluid.

21. A method according to claim 20, wherein:
the using the peak power and resonant frequency comprises using a lookup chart that relates the peak power and resonant frequency to the indication of at least one of a water fraction, a hydrocarbon fraction, water conductivity, and water salinity of the fluid.

22. A method according to claim 20, wherein:
the using the peak power and resonant frequency comprises using a cross-plot that relates the peak power and resonant frequency to the indication of at least one of a water fraction, a hydrocarbon fraction, water conductivity, and water salinity of the fluid.

23. A method according to claim 20, wherein:
the using the peak power and resonant frequency comprises using a cross-plot that relates the peak power and resonant frequency to an indication of water conductivity.

24. A method according to claim 23, wherein:
the using the peak power and resonant frequency further comprises using the indication of water conductivity and at least one of the peak power and resonant frequency with a second cross-plot that relates the water conductivity and the at least one of the peak power and resonant frequency with an indication of water fraction.

25. A method according to claim 20, wherein:
the resonator is loop-gap resonator.

26. A method according to claim 25, wherein:
the loop-gap resonator is a double loop-gap resonator defining first and second cylinders and a gap coupling the first and second cylinders, with the chamber extending through the first cylinder and the multiple microwave frequencies being injected into the second cylinder.

27. A method according to claim 20, wherein:
the multiple microwave frequencies are in a range of approximately 10 MHz frequencies at approximately 1 GHz.

28. A method according to claim 20, wherein:
the first chamber is a flow line with a diameter less than approximately 2 cm.

* * * * *